United States Patent
Maclure et al.

(10) Patent No.: US 11,642,124 B2
(45) Date of Patent: May 9, 2023

(54) REINFORCED BRIDGE SUPERELASTIC BONE COMPRESSION STAPLE AND INSERTER SYSTEM

(71) Applicant: ORTHO SOLUTIONS HOLDINGS LIMITED, Littleton, CO (US)

(72) Inventors: Alister Maclure, Chelmsford (GB); Kevin Stamp, Chapeltown Sheffield (GB); Dustin Ducharme, Littleton, CO (US); Nii Armah, Bishop's Stortford (GB)

(73) Assignee: ORTHO SOLUTIONS HOLDINGS LIMITED, Littleton, CO (US)

( * ) Notice: Subject to any disclaimer, the term of this patent is extended or adjusted under 35 U.S.C. 154(b) by 2 days.

(21) Appl. No.: 17/348,308

(22) Filed: Jun. 15, 2021

(65) Prior Publication Data
US 2021/0386422 A1    Dec. 16, 2021

Related U.S. Application Data

(60) Provisional application No. 63/039,638, filed on Jun. 16, 2020.

(51) Int. Cl.
*A61B 17/064* (2006.01)
*A61B 17/068* (2006.01)

(52) U.S. Cl.
CPC ........ *A61B 17/0642* (2013.01); *A61B 17/068* (2013.01); *A61B 17/0644* (2013.01); *A61B 17/0682* (2013.01); *A61B 17/0684* (2013.01); *A61B 2017/0641* (2013.01); *A61B 2017/0645* (2013.01); *A61B 2017/0646* (2013.01)

(58) Field of Classification Search
CPC . A61B 17/0642; A61B 17/0682; A61B 17/10; A61B 17/17; A61B 17/7044; A61B 17/0644; A61B 17/068; A61B 17/0684; A61B 17/076; A61B 2017/0641; A61B 2017/0645; A61B 2017/00668; A61B 2017/0646; A61B 2017/0688
USPC .......................................................... 606/75
See application file for complete search history.

(56) References Cited

U.S. PATENT DOCUMENTS

| | | |
|---|---|---|
| 3,741,205 A | 6/1973 | Markolf |
| 4,152,920 A | 5/1979 | Green |
| 4,269,180 A | 5/1981 | Dall |
| 4,278,091 A | 7/1981 | Borzone |
| 4,394,864 A | 7/1983 | Sandhaus |
| 4,821,721 A | 4/1989 | Chin et al. |
| 5,209,756 A | 5/1993 | Seedhom |
| 5,350,400 A | 9/1994 | Esposito |
| 5,497,933 A | 3/1996 | DeFonzo |
| 5,593,421 A | 1/1997 | Bauer |

(Continued)

*Primary Examiner* — Marcela I. Shirsat
(74) *Attorney, Agent, or Firm* — Hudak, Shunk & Farine Co. LPA (57) ABSTRACT

The invention is a staple comprising a bridge member having a top surface and an opposing bottom surface defining a thickness between and two lateral edges defining a width therebetween and either the thickness or the width includes a center flared area, such as a "diamond-like" shape meaning that it has a v-shape on opposing lateral edges flanked by opposing fillets to form an inserter mount area and the staple has a pair of legs spaced apart along the axis and each joined at a rounded flared shoulder to the bridge member. In a four-legged version the bridge has a waist.

9 Claims, 14 Drawing Sheets

(56) References Cited

U.S. PATENT DOCUMENTS

| | | | |
|---|---|---|---|
| 5,662,655 A | 9/1997 | Laboureau | |
| 5,695,524 A | 12/1997 | Kelley et al. | |
| 5,715,987 A | 2/1998 | Kelley et al. | |
| 6,059,787 A | 5/2000 | Allen | |
| 6,083,242 A | 7/2000 | Cook | |
| 6,325,805 B1 | 12/2001 | Ogilvie | |
| 6,336,928 B1 | 1/2002 | Guerin | |
| 6,348,054 B1 | 2/2002 | Allen | |
| 6,755,831 B2 | 6/2004 | Putnam | |
| 6,783,531 B2 | 8/2004 | Allen | |
| 7,214,232 B2 * | 5/2007 | Bowman | A61B 17/068 606/232 |
| 7,481,830 B2 | 1/2009 | Wall | |
| 7,556,647 B2 | 7/2009 | Drews | |
| 7,572,276 B2 | 8/2009 | Lim | |
| 7,648,514 B1 | 1/2010 | Nakao | |
| 7,867,265 B2 | 1/2011 | Beutter | |
| 8,021,389 B2 | 9/2011 | Molz, IV | |
| 8,235,995 B2 | 8/2012 | Focht et al. | |
| 8,584,853 B2 | 11/2013 | Knight et al. | |
| 8,596,514 B2 | 12/2013 | Miller et al. | |
| 8,628,533 B2 | 1/2014 | Graham | |
| D705,930 S * | 5/2014 | Cheney | D24/145 |
| 8,721,646 B2 | 5/2014 | Fox | |
| 8,728,131 B2 | 5/2014 | Di Giacomo | |
| 8,808,294 B2 | 8/2014 | Fox et al. | |
| 8,821,508 B2 | 9/2014 | Medoff | |
| 9,017,331 B2 | 4/2015 | Fox | |
| 9,034,037 B2 | 5/2015 | Fiere | |
| 9,095,338 B2 | 8/2015 | Taylor et al. | |
| 9,101,349 B2 | 8/2015 | Knight et al. | |
| 9,101,421 B2 | 8/2015 | Blacklidge | |
| 9,204,932 B2 | 12/2015 | Knight et al. | |
| D748,258 S | 1/2016 | Gledel | |
| 9,433,452 B2 | 9/2016 | Weiner | |
| 9,561,032 B2 | 2/2017 | Shelton, IV | |
| 10,004,603 B2 | 6/2018 | Appenzeller | |
| 10,299,842 B2 | 5/2019 | Hollis | |
| 10,792,081 B2 | 10/2020 | Weiner | |
| 10,987,101 B2 | 4/2021 | Ducharme et al. | |
| 11,246,588 B2 | 2/2022 | Maclure et al. | |
| 2002/0173793 A1 | 11/2002 | Allen | |
| 2003/0028218 A1 | 2/2003 | Bauer | |
| 2004/0073222 A1 | 4/2004 | Koseki | |
| 2007/0233113 A1 | 10/2007 | Kaelblein | |
| 2008/0161808 A1 | 7/2008 | Fox | |
| 2009/0318977 A1 | 12/2009 | Di Giacomo | |
| 2010/0063506 A1 | 3/2010 | Fox et al. | |
| 2012/0228355 A1 | 9/2012 | Combrowski et al. | |
| 2013/0026206 A1 | 1/2013 | Fox | |
| 2013/0041406 A1 | 2/2013 | Bear et al. | |
| 2013/0206815 A1 | 8/2013 | Fox | |
| 2013/0231667 A1 | 9/2013 | Taylor et al. | |
| 2013/0331839 A1 | 12/2013 | Hester et al. | |
| 2014/0014553 A1 | 1/2014 | Knight et al. | |
| 2014/0018809 A1 | 1/2014 | Allen | |
| 2014/0020333 A1 | 1/2014 | Knight et al. | |
| 2014/0034702 A1 | 2/2014 | Miller et al. | |
| 2014/0097228 A1 | 4/2014 | Taylor et al. | |
| 2014/0154236 A1 | 6/2014 | Hester | |
| 2014/0277516 A1 | 9/2014 | Miller et al. | |
| 2014/0358187 A1 | 12/2014 | Taber | |
| 2016/0235460 A1 | 8/2016 | Wahl | |
| 2017/0007305 A1 | 1/2017 | Hollis et al. | |
| 2017/0065275 A1 * | 3/2017 | Cheney | A61B 17/064 |
| 2017/0100163 A1 | 4/2017 | Palmer et al. | |
| 2017/0181779 A1 | 6/2017 | Leither | |
| 2017/0209192 A1 | 7/2017 | Krauss | |
| 2017/0231625 A1 | 8/2017 | Handie | |
| 2017/0281157 A1 | 10/2017 | Hartdegen et al. | |
| 2017/0303978 A1 | 10/2017 | Palmer | |
| 2018/0289366 A1 | 10/2018 | Morgan et al. | |
| 2018/0353172 A1 | 12/2018 | Hartdegen et al. | |
| 2019/0046182 A1 | 2/2019 | Krumme | |
| 2019/0192140 A1 | 6/2019 | Ducharme | |
| 2019/0192160 A1 | 6/2019 | Stamp | |
| 2019/0231349 A1 | 8/2019 | Wahl et al. | |
| 2019/0282231 A1 | 9/2019 | Vasta | |
| 2020/0000464 A1 | 1/2020 | Gaston et al. | |
| 2020/0008807 A1 | 1/2020 | Hollis | |
| 2020/0038076 A1 | 2/2020 | Amis et al. | |
| 2020/0100820 A1 | 4/2020 | Hollis et al. | |

\* cited by examiner

REINFORCED BRIDGE SUPERELASTIC BONE COMPRESSION STAPLE AND INSERTER SYSTEM

FIELD OF THE INVENTION

The present invention relates to a room temperature superelastic bone compression staple and staple inserter system intended for bone fixation in the surgical management of fractures and reconstruction of the foot and hand, and more specifically, the staple is a two-legged staple with an improved bridge and shoulder configuration to distribute loading in insertion and use.

BACKGROUND OF THE INVENTION

Initial bone staples were temperature activated memory staples, which were rendered obsolete through the adoption of mechanically activated room temperature superelastic Nitinol devices as the relevant materials technology advanced to the current state of the art.

Over 1.8 million orthopaedic trauma fixation procedures were performed in the US in 2016, which is expected to remain the fastest growing segment through to 2025 and is expected to reach over $4 billion by 2025, and the fastest growing part of this market is the staple fixation segment. The primary driver for growth is reportedly a reduced operating time as compared to screws, and plates.

While this growth demonstrates that orthopedic arts have accepted bone staples as an alternative and even a preferred fixation hardware to screws and bone plates for certain procedures, there remain issues and limitations to the designs presently available. While the latest generation of memory staples have improved rigidity and compressive capability when used alone or as adjunctive hardware, (which could improve outcomes for certain procedures, such as the Lapidus arthrodesis), it is still desirable to provide a stiffer and stronger construct and more reproducible surgical technique than the generally accepted perpendicular arrangement of legs and bridge used for example for a first metatarsophalangeal arthrodesis procedure. Additionally, the prior art devices are not optimal for fracture and osteotomy fixation of the hand and foot, including joint arthrodesis and to stabilize and dynamically compress bone fragments to facilitate osteosynthesis.

In response to these and other concerns, the present staple has a low-profile design to respect the economy of space in small bone procedures and further is designed for quick and efficient use, including removal following bone fusion. As used herein, "low-profile" means that the staple includes a bridge member having a bottom surface that is so close as possible, and may contact the bone. In addition, the staple has shoulders between the legs and bridge that flares to distribute force unto the underlying bone at this point.

Additional issues with the prior art staples include problems with packaging, implant or instrument breakage (including shearing of the legs or fracture at the bridge member), incompatibility with the staple inserter or other related instruments, lack of compression or sustained compression within the bone/implant construct, and difficulties with the instrument and implantation process.

A known risk with the prior art staples is associated with over-spreading the staple, which can over-stress the staple legs and have a deleterious effect on mechanical properties, recoverable strain and fatigue resistance. As the art has dealt with this problem, other risks associated with bridge strength have arisen. The present invention reduces this risk through design improvements achieved in design of the leg/bridge interface, i.e. at the "shoulders" of the staple, as well as for the bridge member itself through the addition of a thickened area or "node, flanked on either side by narrowed areas or "fillets" or waists". In the present invention, a sinuous configuration provides that the shoulders flare in width and thickness out of the legs and into the bridge to form a "hood" at the shoulder which wraps the bone. The bridge narrows into a first and second waist, which have a width and thickness similar to the legs, and which then flare outward again to the thickened area which forms opposing nodes that together form the two apexes of a "diamond" (although the points may be rounded to avoid stress points).

The present staple has a unique configuration that addresses the issues of breakage while providing a low profile implant that is particularly well suited for small bone procedures. The staple and staple inserter are designed to first hold the staple in position for insertion and then to function together to avoid over-spreading and/or misalignment of the staple legs so as to reduce potential use risks and to provide a device which is inherently less prone to user error. In addition, the staple is designed for permanent implantation or unlike prior art devices, for removal following bone fusion which can typically take 4-6 weeks while the patient is partially weight bearing. Specific instrumentation is provided for the removal procedure.

The staple will be manufactured from ASTM F2063 room temperature superelastic (e.g., from 2 to up to 8%) Nitinol. (and it will be understood that other shape memory materials can be used in this design).

SUMMARY OF THE INVENTION

The present invention relates to a superelastic Nitinol staple having a pair of spaced legs joined by a bridge member is "straight-backed" meaning that it extends along an axis to form a "table-top" type of configuration more notable in the energized state in which the legs are substantially transverse to the bridge member, however, with a rounded top surface. In fact, the top surface can be advantageously curved in one or two dimensions, i.e., along the axis and transverse to it to provide a segment of a sphere or torroid, especially when the legs are in the converging position. This provides a staple having a low profile straight-backed configuration which suits implantation in the small bone environment, in particular for use in osteotomies, fusions or other osteo synthesis procedures.

The staple is fabricated by machining a blank to form a staple in the closed (converging legs) shape and the resulting staple is mechanically deformed during use to induce the superelastic shape memory properties to compress bone segments and facilitate osteosynthesis. Alternatively, the staple can be formed as a flat straight bi-laterally symmetrical (about both the medial and the longitudinal axes) blank with an intermediate area including three thickened areas, one to form either shoulder at the bridge leg bend, and one in the middle of the bridge. After forming, the legs are bent on either side to form the U-shaped configuration.

The staple has a bridge member preferably having an optimal configuration with a thickness defined between an exterior and corresponding opposing interior surface and a width defined between two side edges, and where one of the thickness and the width have a thickened or reinforced area provided by a flare or swelling of material such as to form an edge member with a profile that is a serpentine or a half diamond shape with fillets on either side of a v or bump. The opposing edge members flare at the same point along the length of the bridge to form symmetrical profiles. The result is the formation of a partial diamond flanked by two narrower straits that widen again into the shoulder area. This reinforcement serves to inhibit the potential for failure at the bridge.

The legs may be joined to the bridge member by corner extensions or "shoulders" which flow into the legs or may extend directly from the bridge for example from an inwardly curved recess in the ends of the bridge member. The legs preferably have a uniform cross-sectional shape which helps to eliminate stress risers, for example, at the conjunction of the legs and bridge. The bridge and shoulders are "tuned" to optimize stress. Once past the shoulder region, the legs generally are uniform cross-section due to ease of mfg. The invention could further include legs that widen at the bottom to form a paddle for osteoporotic applications. The staple is designed for optional removal, so that while the staple may include texturing, ridges, or barbs to improve the hold in bone, the amount of mechanical interference is limited, for example by the provision of low ridges and on one only one or two surfaces of the legs, such as on the inner surface facing inward on the leg. Thus, the staple design permits easy removal.

The staple is provided having a range of different bridge lengths and various leg lengths in the same range of length, so as to accommodate different fixation procedures in the forefoot, midfoot, rearfoot and hand. The staple is typically provided in sizes in which the dimensions of the bridge are 10 to 25 mm in length; 1 to 6 mm and preferably 1.5 to 5 mm in width; with a maximum width at the node of 2.5 to 6 mm, and preferably 3 to 4 mm; and with a minimum width on either side of the node of 1.5 to 3 mm and preferably 2.2 to 2.6 mm, and having leg lengths of 5 to 20 mm, and preferably of 7.5 to 15 mm, with staple being provided at integrals of 3 mm bridge and leg lengths.

In addition, the staple is part of a system with includes a staple inserter, and where the bridge reinforcement helps to hold the staple on the inserter. The staple can be supplied pre-assembled on an inserter or introducer in a sterile procedure pack containing disposable instrumentation.

DETAILED DESCRIPTION OF THE INVENTION

Figure 1:
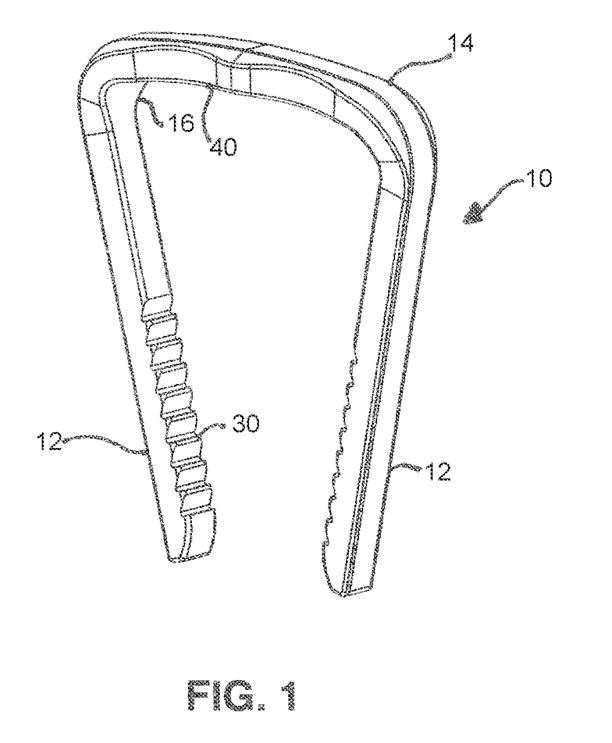
FIG. 1 shows a top perspective view of the staple with the legs in a converging state and in accordance with the present invention.
Figure 2:
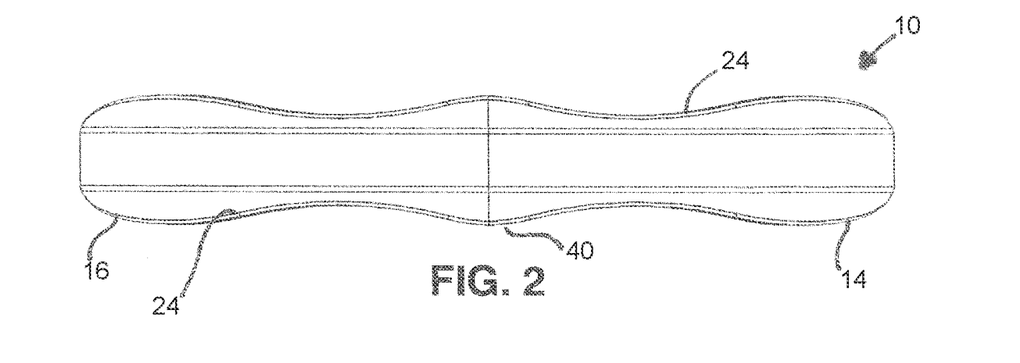
FIG. 2 shows a top view of the staple of FIG. 5.
Figure 3:
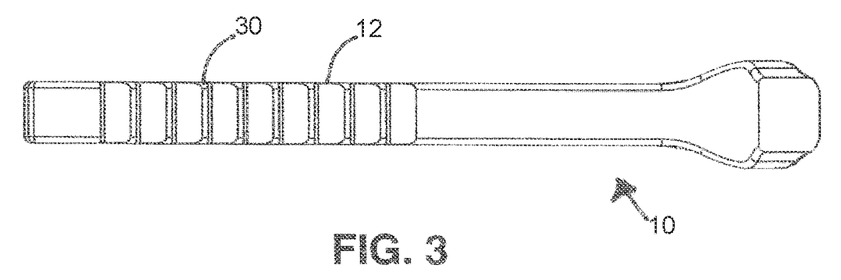
FIG. 3 shows a first side view of the staple of FIG. 2 with a cross section of the narrow section of the bridge as shown in FIG. 2.
Figure 4:
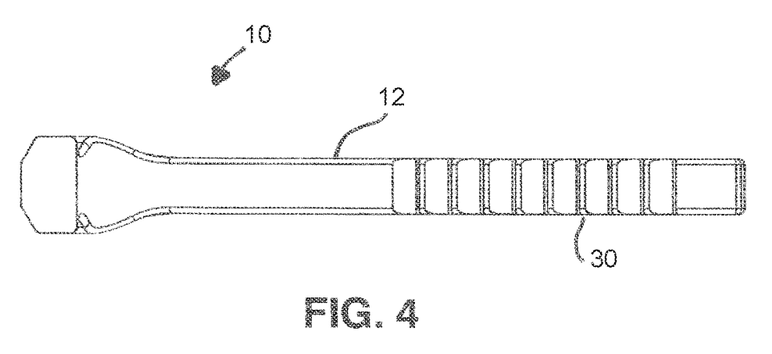
FIG. 4 shows a second side view of the staple of FIG. 2 with a cross section of the thickened section of the bridge as shown in FIG. 2.
Figure 5:
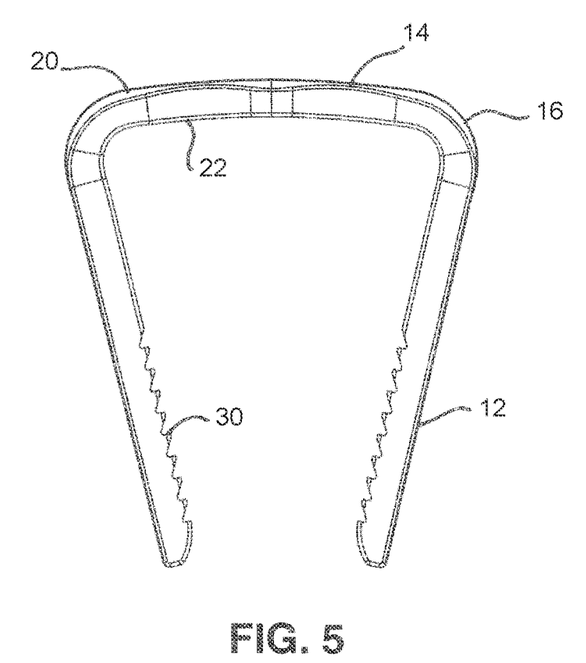
FIG. 5 shows a side view of the staple of FIG. 1.
Figure 6:
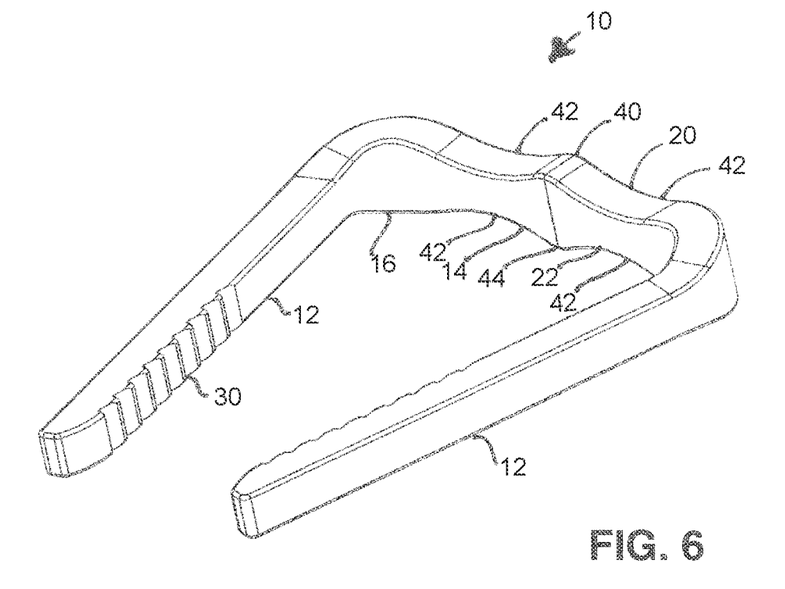
FIG. 6 shows a bottom side perspective of the staple of FIG. 1.
Figure 7:
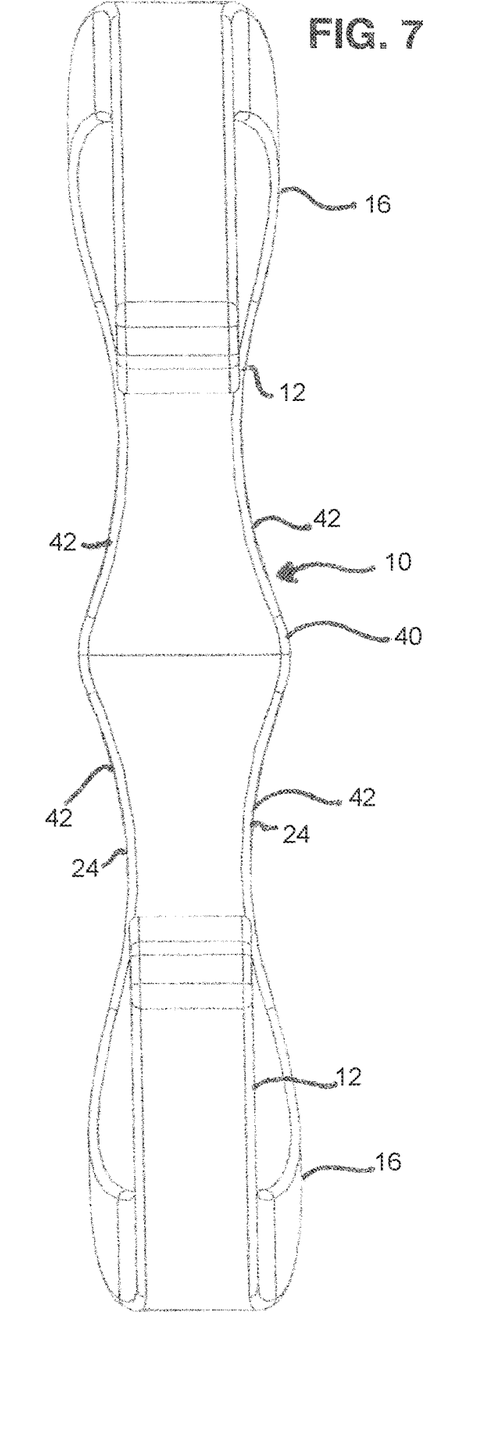
FIG. 7 shows a bottom detail view of the staple of FIG. 1.
Figure 8:
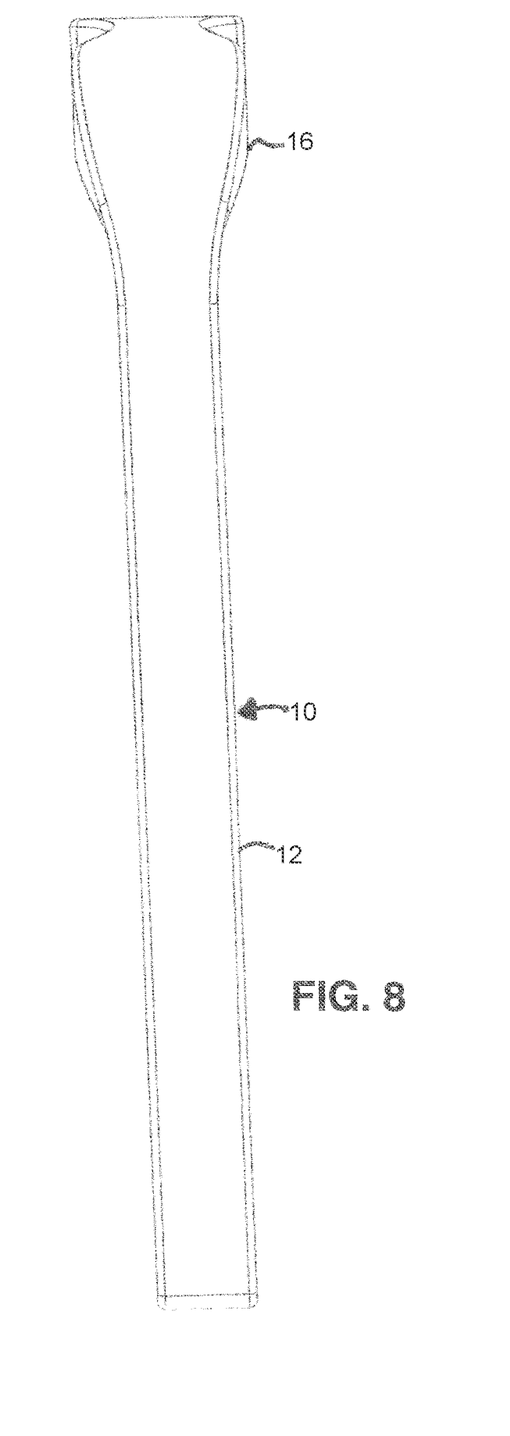
FIG. 8 shows a side view of the staple of FIG. 1.

The present invention relates to a room temperature superelastic Nitinol bone compression staple 10. The staple 10 has two or more legs 12 that will engage bones or bone segments through the cortical surfaces. The legs 12 are spaced apart from each other and joined together by bridge member 14 that extends across the area between legs at either end of the bridge member 14. As shown, the legs are joined to transitional areas 16 or shoulders which flare outward in width compared to the width of the leg and of the bridge to which they join and fold or curve at an angle of from 75° to 90°, and preferably from 85° to 90° relative to a long axis of the bridge member 14 to form a hood shape as can be seen in FIGS. 6-8.

The bridge member 14 has a top surface 20 and a bottom surface 22 which have corresponding shapes so that they are separated by a constant thickness for at least a portion, and preferably for at least 50%, and more preferably for at least 75% or even 90% of the surface area and further has a complex curving configuration. It extends along an axis preferably in a straight profile, but with a topography that can curve in either of two dimensions (i.e. length and width) or in both of two transverse directions. The shape includes two side edges 24, which have the complex curving shape (which looks somewhat like a curly bracket "{") of the present invention.

The bridge member 14 includes a thickened or reinforced area 40 provided by a flare or swelling of material such as to form an edge member with a profile that is a serpentine or a half diamond shape with fillets or concave curves 42 on either side of a node, v-shape or bump 44. The opposing edge members flare at the same point along the length of the bridge to form symmetrical profiles. The result is the formation of a partial diamond 46 flanked by two narrower straits 48 that widen again into the shoulder area. This reinforcement serves to inhibit the potential for failure at the bridge.

The surfaces extending between the side edges 24 forming the top or outer surface 20 and the bottom or inner surface of the bridge 22 curve along the axis, in a shape that may define a portion of a circle, and they curve as well in a direction transverse to the axis. Preferably the bridge curves along the length. It is also possible that the bridge curves along the width. In this instance, both curves are convex relative to the bottom surface and can be the same or different radius curves. Preferably, the curves have the same inner radius dimensions so that the bridge member defines portions of spheres on the outer and inner surfaces and the radius is between 10-100 mm, and optimally is 50 mm +/−10 mm.

The legs 12 also have a regular shape. While this can be a rectangle, they can form other polygons in cross section. The legs may also include features 30 to help hold the legs in the bone, such as texturing, or ridges or barbs that help to hold the legs in position. Preferably, the surfaces of the legs that include this feature are opposing surfaces, such as surfaces that face an opposing leg as shown in the detail of FIG. 6. These ridges may include a series of spaced parallel ridges or alternating areas which in cross-section extend away from the base surface of the leg and return the base surface of the leg. Alternatively, the legs may include a series of grooves cut into the surface, or the legs may have a surface treatment, such as knurling, or cross-hatching. If they have ridges, the ridges may cover a portion of the vertical surface, such as 10-90%, and preferably from 25-50%. The ridges are lower profile than barbs, (for example only 0.25-2, and preferably 1+/−0.25 mm in height from the surface of the leg in order to permit earlier staple re-orientation and increased bone growth after removal.

a pair of opposing legs, either one or two legs may include these features. The legs have a cross-sectional configuration that provides for improved resistance to breaking as well as increased compressive forces, such as a polygonal shape that is not square. One preferred configuration is a rectangle. The staple may have two opposing legs, spaced apart from each other along the axis of the bridge member, or on one side it may have two legs, and one on the other, or optionally, it may have four legs which are situated to form a rectangle which circumscribes the bridge member. The staple is provided having a range of different bridge widths ranging from 10 mm to 25 mm and various leg lengths in the same range of length, so as to accommodate different fixation procedures in the forefoot, midfoot, rearfoot and hand.

Figure 20:
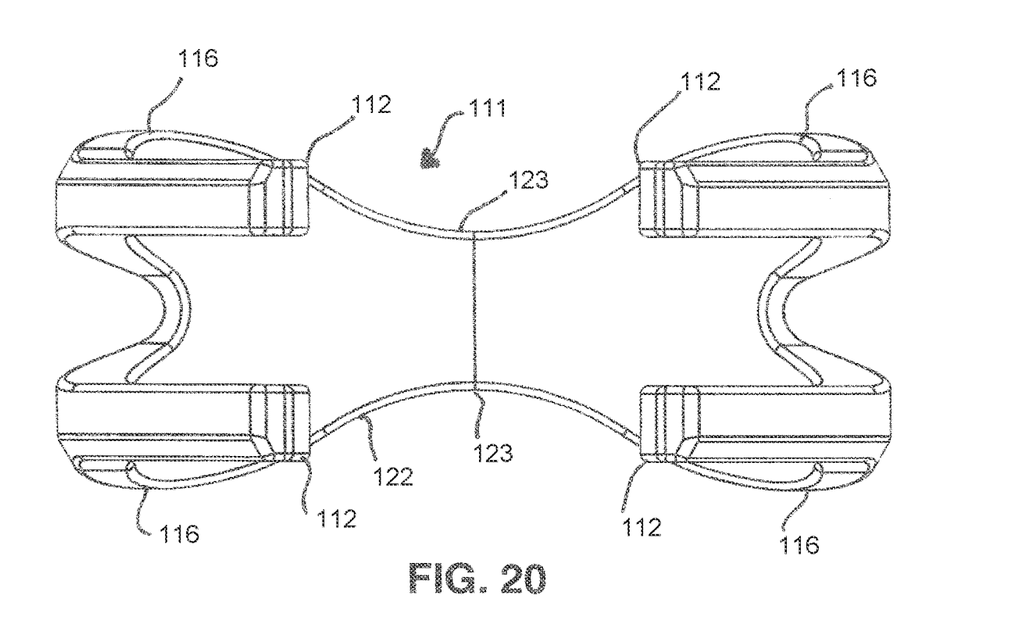
FIG. 20 shows a bottom view of the staple of FIG. 18.
Figure 21:
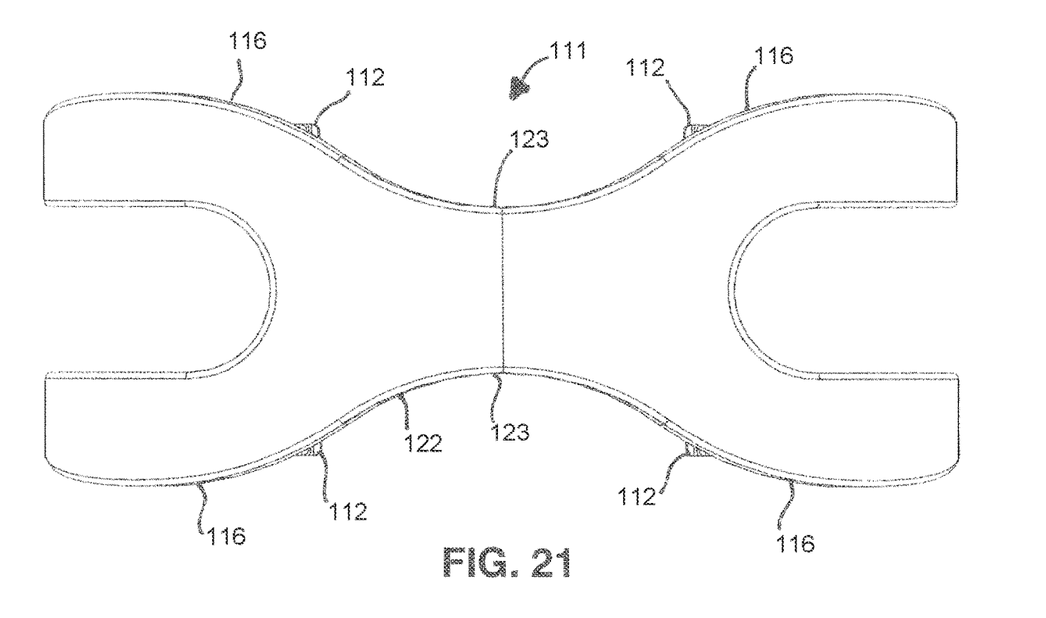
FIG. 21 shows a top view of the staple of FIG. 18.

FIGS. 18-21 illustrate a four-legged version 111 of the staple of the present invention. This staple has a bridge 122 which joins four legs 112 which may include the ridges 120 of the two-legged version of the staple. This version of the staple includes the hooded shoulder members or flares 116 which join each of the legs to the bridge which has a central inward curve to accommodate the sliding relationship with the inserter rails that have opposing convex curves to capture the inward curves of the bridge member. Thus, the bridge has a central waist area 123 that functions to interact with the inverse curved surfaces of the inserter rails to guide the staple along that length. FIG. 20 shows the complex topography which forms the reinforcing attributes of the shoulder members.

Figure 9:
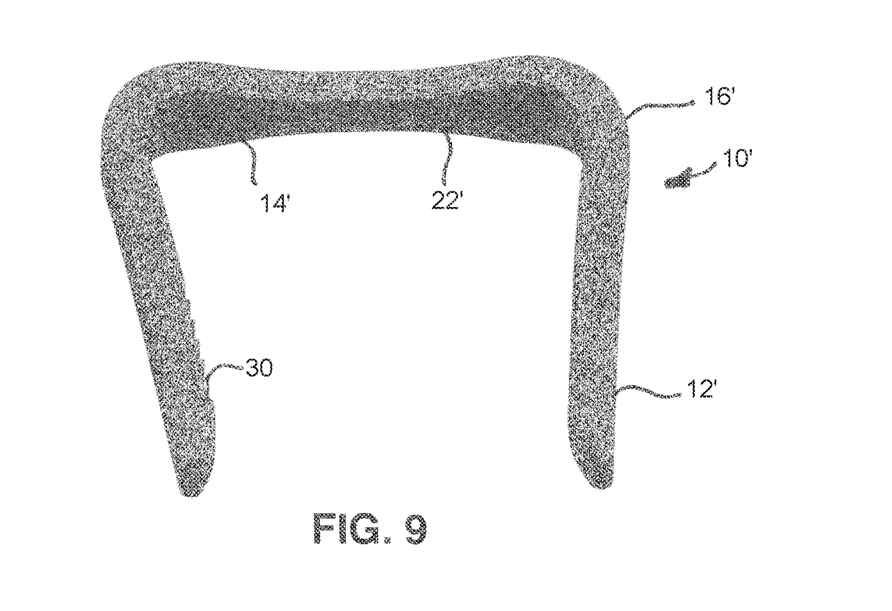
FIG. 9 shows a bottom perspective view of a staple in the activated state with the legs in parallel position and having shoulder optimization in accordance with the present invention.
Figure 10:
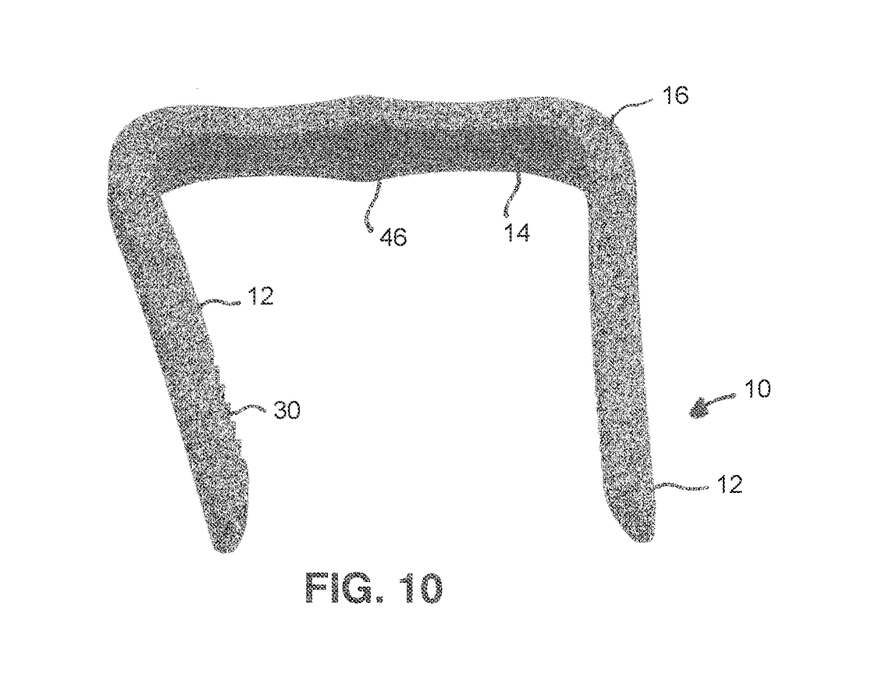
FIG. 10 shows a bottom perspective view of a staple in the activated state with the legs in parallel position and having bridge and shoulder optimization in accordance with the present invention.
Figure 11:
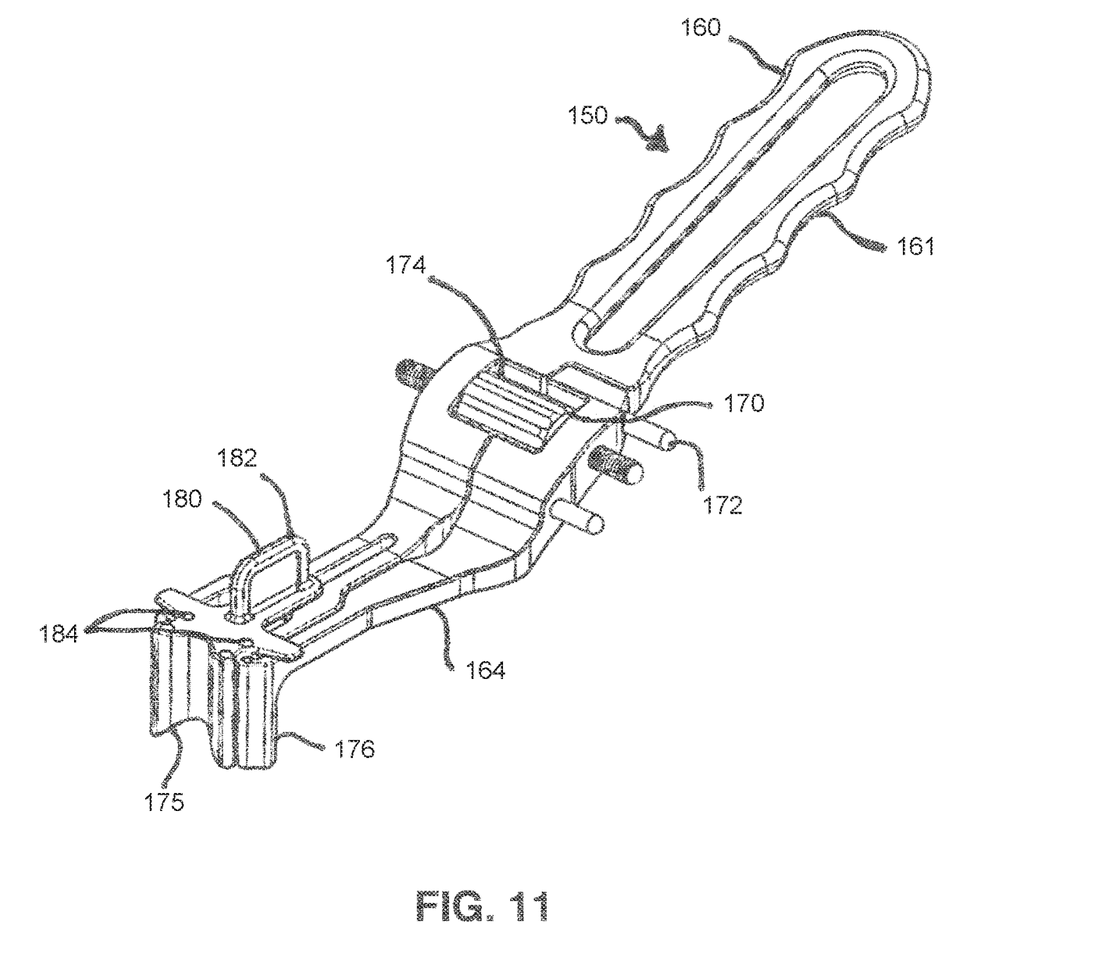
FIG. 11 shows side perspective of a drill guide body for the implantation of a four-legged staple in accordance with the present invention.

FIGS. 9 and 10 illustrate finite element analysis that demonstrates the advantages of the staple 10, 10' of the present invention. FIG. 9 only having the flared optimized shoulders 16' as a transition between the bridge 14' and the legs 12', while FIG. 10 also includes the diamond area 44.

Figure 12:
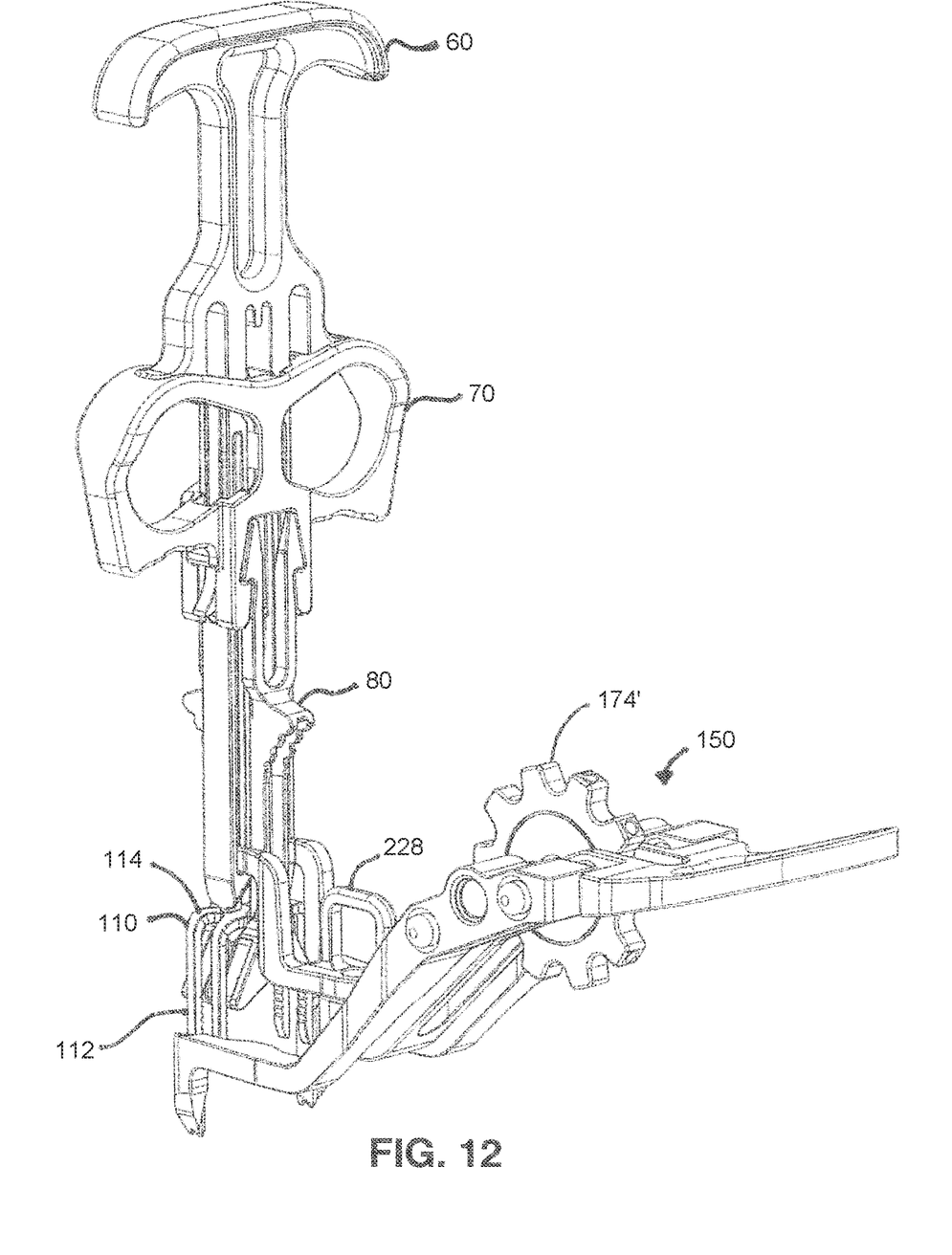
FIG. 12 shows a side perspective view of a staple inserter loaded with a four-legged staple for use in the drill guide body and with the inserter system of the present invention.
Figure 17:
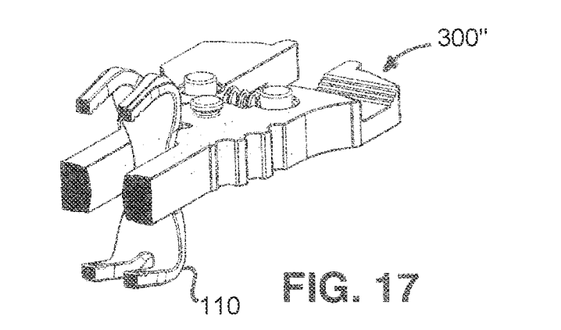
FIG. 17 shows an alternative inserter staple cartridge member with truncated legs and loaded with a four-legged staple for use with the inserter system of the present invention.
Figure 18:
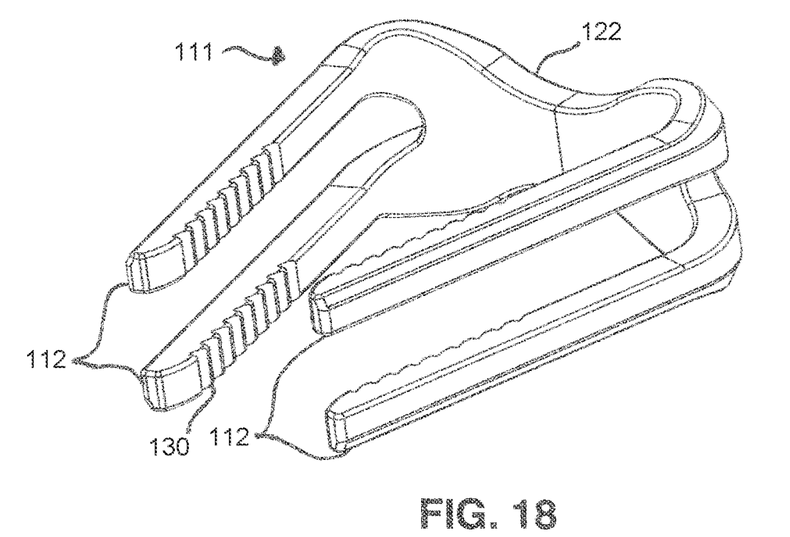
FIG. 18 shows a bottom side perspective of a four-legged staple in accordance with the present invention.
Figure 19:
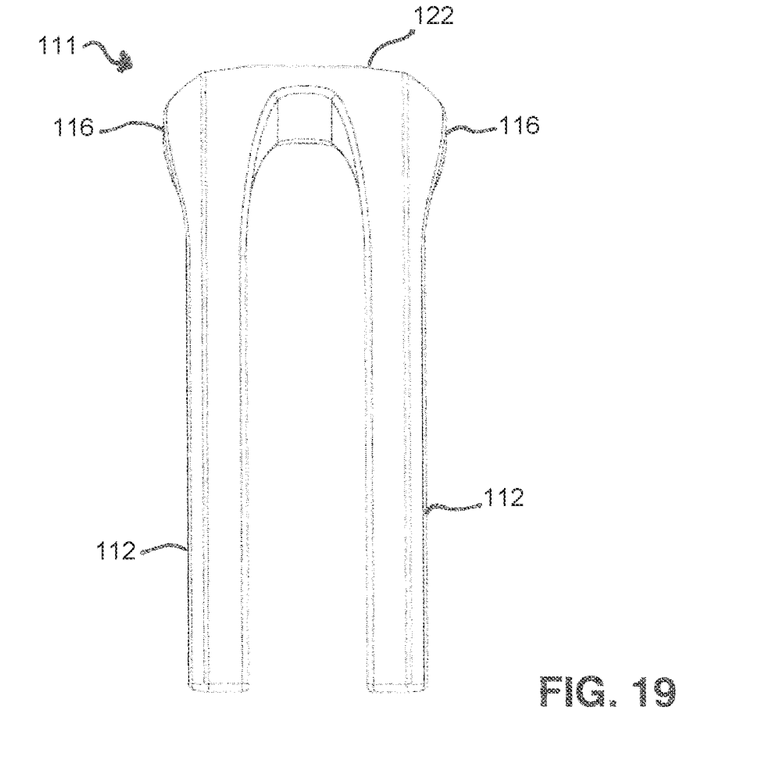
FIG. 19 shows a side view of the staple of FIG. 18.

The staple system of the present invention also comprises a companion four-legged staple 111, shown on a further embodiment of the inserter cartridge 80 in FIG. 12 as well as in FIGS. 17 and 18 that illustrate the hooded shoulder feature and curving bridge member of the present invention on a multi-legged staple member. The inserter cartridge 80 fits on an inserter body and activator member 70 with handle 60 and used with a drill guide assembly 150 having a variation of the turn member 174'. This version is also shown with an additional component 228 that inserts into a bore in the drill guide and has arms that secure and stabilize the inserter during the implantation of the staple into the pre-drilled bores. The four-legged staple includes legs 112 and a bridge member 114 that may also include the bridge optimization of the present invention.

Figure 13:
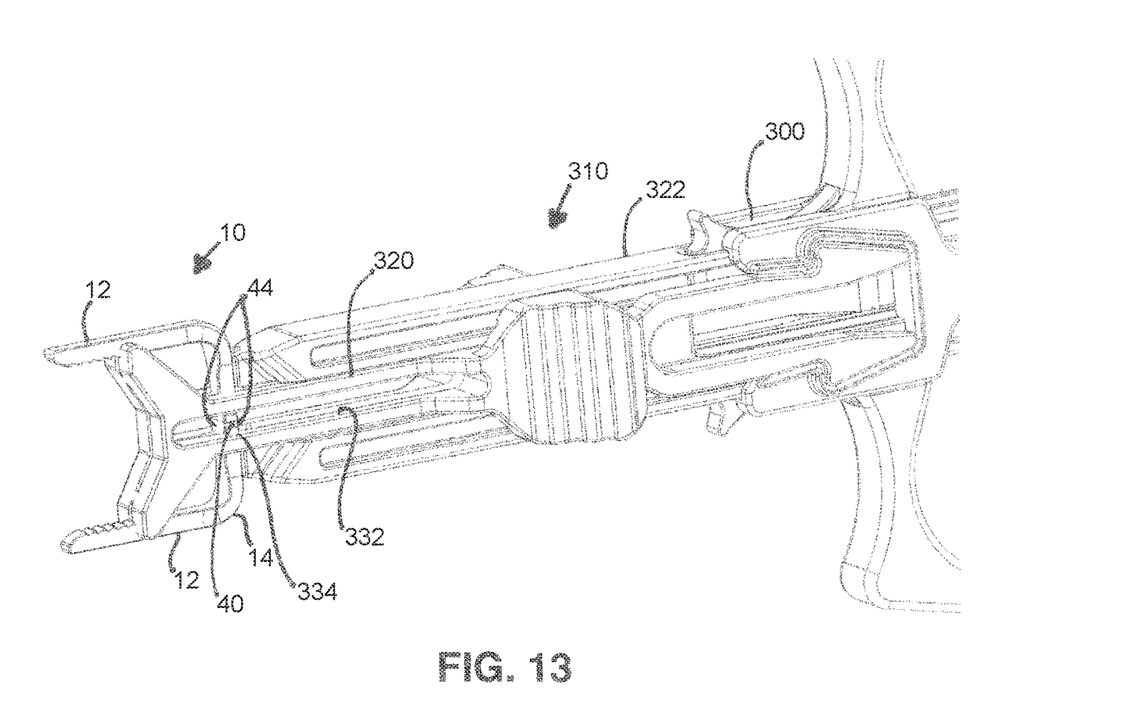
FIG. 13 shows a side perspective view of an inserter staple cartridge member loaded with a two-legged staple in an activated state ready for use with the inserter system of the present invention.
Figure 16:
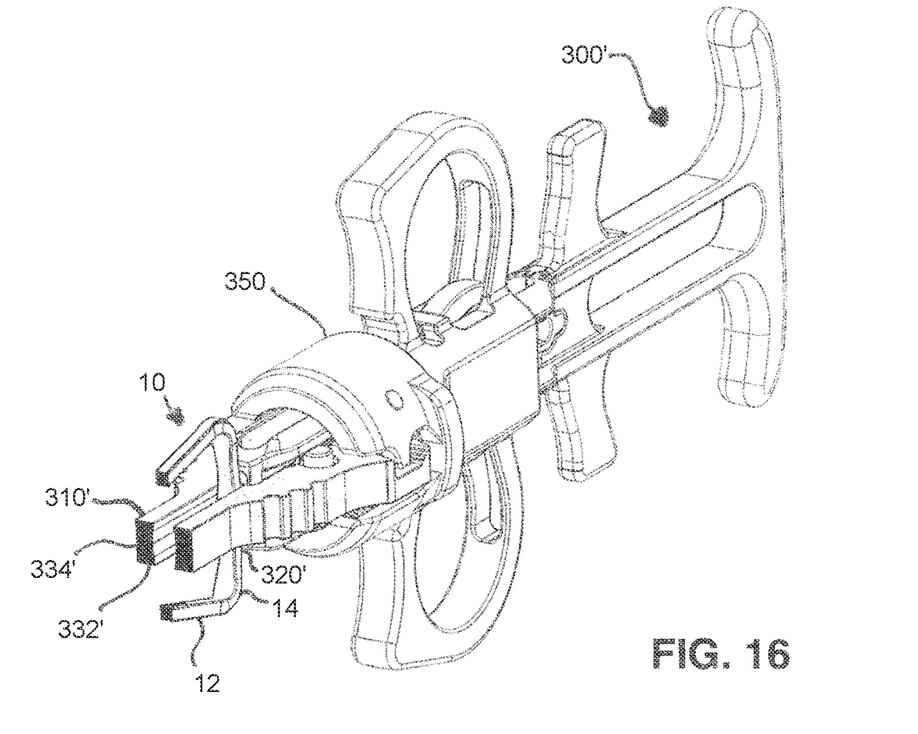
FIG. 16 shows a side perspective view of an inserter staple cartridge member of FIG. 15 loaded with a two-legged staple with the rails of the inserter truncated in order to show the groove members on the inside of the rails to guide the diamond bridge of the staple.

FIGS. 13 and 16 illustrate how the nodes 44 or diamond member 40 of the bridge 14 of the staple 10 of the present invention are constrained and guided along the length of the inserter in mating surfaces such as in a recess, i.e., a slot 332 or a groove '332 formed on the side legs 320 of a staple cartridge 310 on an embodiment of the staple inserter 300 where internal surfaces 334 interface with the area between the fillets 42 and the nodes 44 of the bridge member to secure the staple 10 in the staple inserter cartridge 310 and while the staple legs 12 are held by the end of the staple cartridge 310. In the four-legged version the staple bridge may include the concave surfaces while the cartridge legs include convexly rounded surfaces that hold the waist. FIG. 16 illustrates a further embodiment of the staple inserter and staple cartridge assembly 300' in which the cartridge has a close-pin type capture mechanism for the staple 10, and a collar 350 that holds the cartridge 310' to the inserter 300'.

FIGS. 17-21 illustrate a four-legged version of the invention having the enhanced bridge and shoulder configuration.

Figure 14:
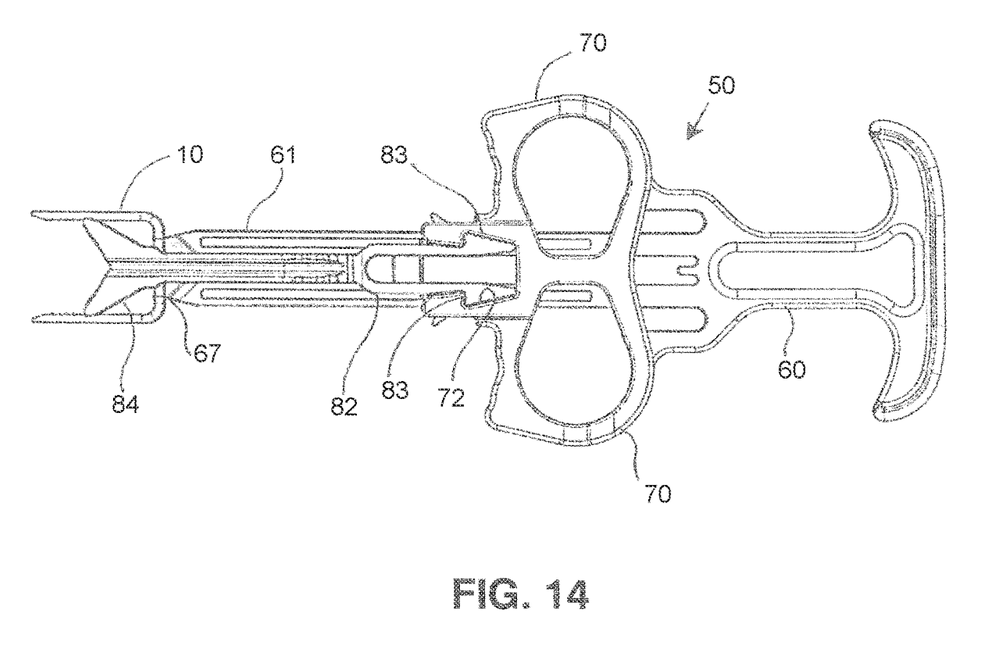
FIG. 14 shows a full side view of the activator member for use with the inserter system of the present invention loaded with a two-legged staple in accordance with the present invention.
Figure 15:
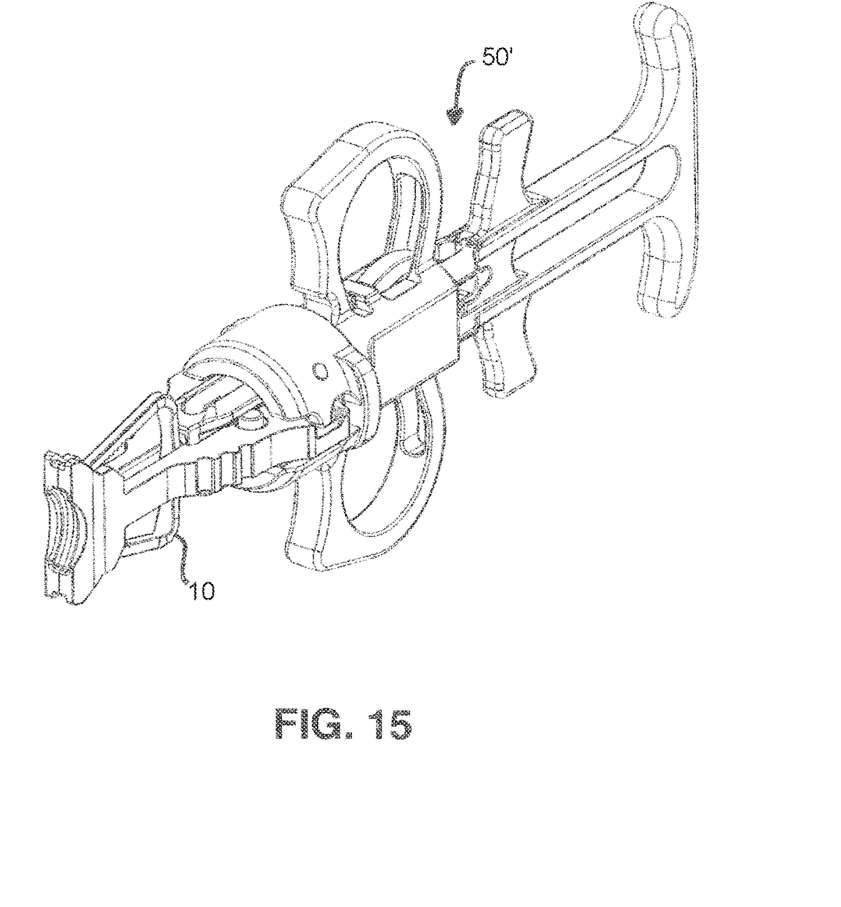
FIG. 15 shows a side perspective detailed view of a further embodiment of the inserted staple cartridge member loaded with a two-legged staple and of the inserted system of the present invention.

FIGS. 12-14 illustrate a drill guide body 200 having a handle 210 and extensions 212 that include grooves 214 that receive drill guide members for a four-legged staple 226 or for a two-legged staple 228 as shown in FIGS. 13 and 14.

Preferably, the staple is fabricated by machining a Nitinol blank to form a staple in the closed (converging legs) shape and the resulting staple is mechanically deformed during use to "load" the staple, meaning to induce the superelastic shape memory properties to compress bone segments and facilitate osteosynthesis. In this state, the staple has legs extending at a substantially transverse direction to the axis of the bridge in order to allow the staple to be inserted into pre-drilled pilot holes in the bone.

Optimally, the staple is supplied pre-assembled and preloaded into a parallel leg configuration on an inserter 110 or introducer in a sterile procedure pack containing disposable instrumentation. In this instance, the inserter 110 has a pair of pivoting handles 120 that are squeezed together to expand a pair of arm member bearing cylindrical holders that bias the staple legs open when the handles are engaged together.

What is claimed is:

1. A staple, comprising:
    a bridge member having a top surface and an opposing bottom surface defining a thickness between and defining a first edge face and a second opposing edge face to define a width between them and the bridge member having a long axis and the first edge face and the second edge face each having a complex curve along the axis so as to form a diamond-like shape widened area between waist areas; and at least one pair of a first leg having a first leg width and a second leg having a second leg width and being spaced apart along the long axis and each leg being joined to the bridge member at a shoulder having a width which is larger than the first leg width and the second leg width.

2. A staple as set forth in claim 1 wherein the superelastic material is Nitinol.

3. A staple as set forth in claim 2, wherein the bridge thickness between the top surface and the bottom surface is constant.

4. A staple inserter system comprising:
a staple, comprising:
a bridge member having a top surface and an opposing bottom surface defining a thickness between and defining a first edge face and a second opposing edge face to define a bridge width between them and the bridge member having a long axis and the first edge face and the second edge face each having a complex curve along the axis so as to form a diamond-like widened area between two waist areas;
at least one pair of legs with a first leg having a first leg width and a second leg having a second leg width and being spaced apart along the long axis and each leg being joined to the bridge member at a shoulder having a width which is larger than the first leg width and the second leg width;
and an inserter that constrains the diamond-like widened area on the bridge of the staple.

5. A staple as set forth in claim 4, wherein at least one of the pair of the legs include an engagement feature.

6. A staple as set forth in claim 4, wherein both legs of the pair of legs includes an engagement feature.

7. A staple as set forth in claim 6, wherein the engagement feature is a plurality of ridges.

8. A staple as set forth in claim 4, wherein the diamond-like widened area includes two opposing rounded v-shapes at a center along the long axis of the bridge member.

9. A staple, comprising:
a superelastic material which includes a bridge member extending along an bridge axis between a first end and a second end defining a bridge length and having a top surface and a bottom surface separated by a thickness defining a first face and a second opposing face which defines a bridge shape having a width which varies along the length and whereby the bridge shape is bilaterally symmetric between the first end and second end about a midplane transverse to the bridge axis and the bridge shape has a maximum width at the mid-point to and includes opposing v-shaped apexes and a minimum width n between the first end and the midplane and a minimum width n between the midplane and the second end whereby the minimum width n is greater than 20% less than the width at the midplane; and
with at least one pair of a first leg having a first leg width and a second leg having a second leg width joined to the bridge member at the first end and the second end.

* * * * *